Nov. 20, 1973
S. B. HUTTON, JR
Plant Pat. 3,410
AZALEA PLANT
Filed April 12, 1972
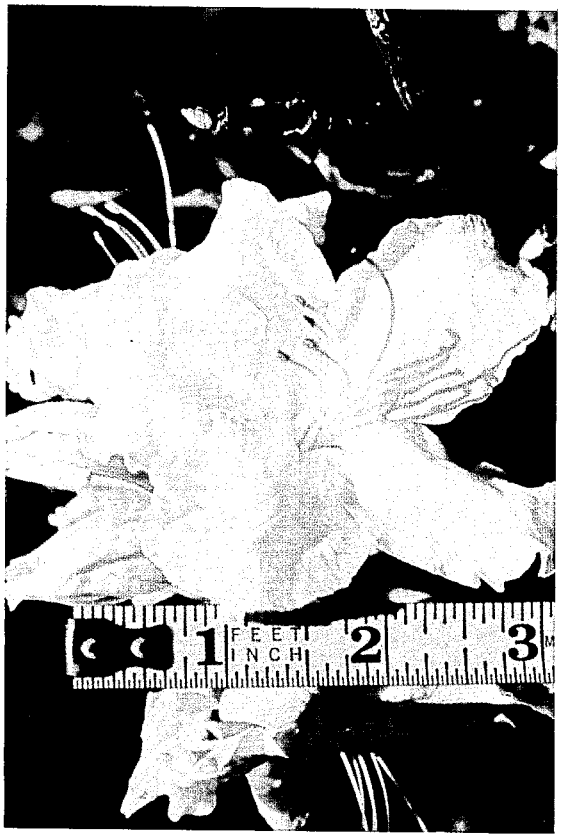
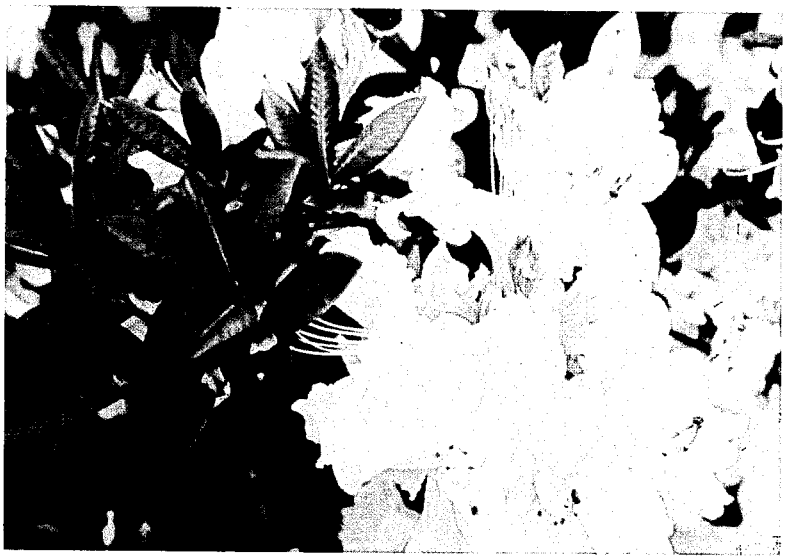

United States Patent Office

Plant Pat. 3,410
Patented Nov. 20, 1973

3,410
AZALEA PLANT

Sidney B. Hutton, Jr., West Grove, Pa., assignor to The Conard-Pyle Company, West Grove, Pa.

Filed Apr. 12, 1972, Ser. No. 243,486
Int. Cl. A01h 5/00
U.S. Cl. Plt.—55 1 Claim

ABSTRACT OF THE DISCLOSURE

An azalea plant having large flowers of bright yellow color, in large trusses and with a blotch of deeper yellow-orange color on the upper petal.

SUMMARY OF THE INVENTION

The present invention relates to a new and distinct variety of azalea plant which was discovered by me growing from open pollinated seed of deciduous Exbury-type azaleas.

The objective of my work, which led to the discovery of this new plant, was to find hardy, deciduous azaleas of new and distinctive color with big trusses composed of large florets of color distinct from what has been previously known.

To achieve my objective, open pollinated seed of Exbury-type azaleas, which are noted for bright colors and large florets, was sown by me during the winter of 1953. The resulting seedlings, upon reaching proper size, were transplanted to give each one room for proper growth and development. In the spring of 1955, those which had grown viborously were planted in nursery beds where they continued to develop and first bloomed in the spring of 1956.

From among several hundred seedlings growing, I selected fourty-eight as having special merit. Of these forty-eight, I was particularly attracted to one because of its bright yellow color, its large trusses—six inches across and with individual florets up to three inches across. I particularly noted the frilled edges of the bright yellow petals which had even color and I noted a blotch of deeper yellow on the inside of the upper petal. This particular plant began to show its bright yellow color about May 12th and hold the color evenly as the florets opened and until they dropped about ten days later. I proceeded to reproduce this plant asexually by cuttings. The characteristics I noted in the original plant came true with succeeding propagation and each plant which developed had all the characteristics of my original discovery.

I also noted a sweet, spicy fragrance, characteristic of azaleas of this type but more pronounced than in most others. The flower trusses were held on stiff, woody stems coming from a freely branched plant of essentially upright habit. Bright green leaves began to appear at the same time the flower opened.

My objective was achieved with the discovery of the unique combination of characteristics which distinguish my discovery from all other varieties of which I am aware, as follows:

(1) New, bright yellow color.
(2) Large trusses—six inches across with individual florets up to three inches across.
(3) Frilled edges of the petals.
(4) Deeper yellow blotch on the inside of the upper petal.
(5) Sweet, spicy fragrance.
(6) Upright, freely branched plant habit with stiff, woody branches.

BRIEF DESCRIPTION OF DRAWINGS

The accompanying drawings show, respectively, a cluster and a single flower of a typical specimen of my new azalea variety, and as depicted in color as nearly true as it is reasonably possible to make the same in a color illustration of this character.

DETAILED DESCRIPTION OF DISCLOSURE

The following is a detailed description of my new variety in which the terminology of the colors corresponds to that of the Horticultural Color Chart of the Royal Horticultural Society, London, England.

Type: Hardy; bush; for garden decoration and general landscaping uses.

Propagation: It does hold its distinguishing characteristics through succeeding asexual propagations by cuttings.

*Flower*

Locality where grown: West Grove, Pa.

Flowers borne: Seven to thirteen, in uneven numbers, in rounded clusters or trusses, on strong, medium stems.

Quantity of bloom: Abundant, outdoors.

Continuity: One season—May 5th to May 25th at West Grove, Pa.

Fragrance: Moderate, sweet, spicy.

*Bud*

Size: Long, slender, medium heavy, erect, Yellow-Green Color Group 144B. Medium rough, numerous hairs: Color Group White 155C.

Form: Before petals open the buds have an inconspicuous neck with numerous hairs one-third of the way up the surface of the bud. Hairs extend beyond the tip of the bud equal to one-tenth of its length.

*Before petal tips separate.*—Color Group Yellow 8A.

*As first petal opens.*—Size: Medium—1¾ to 2 inches long. Form: Pointed. Color: Outside: Color Group Yellow 8A; inside: Color Group Yellow 8B.

Opening: It does open well under all weather conditions.

*Floret*

Size when fully open: Medium, 2¾ inches to 3½ inches.

Petalage: Single, always 5 petals arranged regularly.

Form: Open, cupped at first; becoming open, bell-shaped; petals at first loosely rolled outward; remaining at maturity loosely rolled outward.

Petals: Medium thick, leathery; with inside velvety; outside velvety.

*Shape.*—4 lower petals undulate; to doubly crenate. Center or top petal.—Undulate; and doubly crenate.

The following description of a newly opened flower was made from a flower grown outdoors during May at West Grove, Pa.:

*Four lower petals.*—Color: Outside surface: Color Group Yellow 8B. Inside surface: Color Group Yellow 8B.

*Upper petal.*—Outside surface: Color Group Yellow 8B. Inside surface: Color Group Yellow 8B modified by a characteristic blotch of Yellow-Orange, Group 15B, to Yellow-Orange, Group 14B.

The following description was made from a flower that was open for three days, outdoors in the month of May at West Grove, Pa.:

*Four lower petals.*—Color: Outside surface: Color Group Yellow 8B, turning to Yellow 8C. Inside surface: Color Group Yellow 8B, turning to Yellow 8C.

*Upper petal.*—Outside surface: Color Group Yellow 8B, turning to Yellow 8C. Inside surface: Color Group Yellow 8B, turning to Yellow 8C with the blotch ranging from Color Group Yellow 13B to 13C.

General color effect:

*Newly opened flower.*—Color Group Yellow 8A.

*Three days open.*—Color Group Yellow 8B, turning to Yellow 8C.

Behavior: Petals drop off cleanly.

Flower longevity: Flowers on the plant last 3 to 5 days in May. Cut flowers last 3 to 5 days in May. Flowers grown in greenhouse kept at living room temperatures last from 3 to 5 days in May.

*Reproductive organs*

Stamens: Five on each bloom.

Filaments: All five with anthers. Extend beyond the flower by approximately the same length as the flower.

*Bottom:* Color Group Yellow-Orange 15A.

*Top, just below anthers.*—Color Group Yellow-Orange 15D.

Anthers: All open at once, medium: Color Group Yellow-Orange 15A.

Pollen: Moderate: Color Group Yellow 8B.

Styles: Very long; medium heavy.

Stigma: Color Group Yellow-Green 144A, changing to Color Group Yellow-Green 147B.

Ovaries: All enclosed in receptacle.

Sepals: Permanent; very short, spear-shaped, many fine hairs: Color Group White 155C. Sepals: Color Group Yellow-Green 144B.

*Plant*

Foliage: New foliage appearing at flowering in mid-May at West Grove, Pa.

*Leaves.*—Simple leaves, in normal quantity, small to medium, soft.

*Shape.*—Lanceolate to oblong with narrow base.

*Color.*—Upper surface: Color Group Green 138A. Under surface: Color Group Green 137C.

*Rachis.*—Medium. Upper and under sides: Very hairy: Color Group White 155C.

Growth:

*Habit.*—Bushy, upright, columnar, much branched.

*Growth.*—Free.

*Branches.*—Medium heavy. Color Group Greyed-Orange 165B. Dull.

*Main stems.*—Dull. Color Group Greyed-Orange 165B to 166D.

*New shoots.*—Dull. Color Group Green 137D.

*Hardiness*

Plants growing in sheltered to open locations, without protection, survived severe winter conditions with no injury in a moderate climate at West Grove, Pa.

I claim:

1. A new and distinct variety of azalea plant substantially as herein illustrated and described, characterized particularly as to novelty by a bright yellow color of the bloom which changes only slightly over the life of the flower, with a deeper yellow-orange blotch on the upper petal, frilled edges of the petals, large size of the individual floret which comes in odd numbers from 7 to 13 florets making up a large, firm truss which is borne on upright, stiff, woody stems with bright green foliage appearing as the flower opens, vigorous, well branched plants uninjured by winter or summer temperatures in moderate climate, and by a sweet, spicy fragrance, characteristic of azaleas of this type but more pronounced than in most.

No references cited.

ROBERT E. BAGWILL, Primary Examiner